United States Patent
Spratte, Jr. et al.

(10) Patent No.: US 10,149,805 B2
(45) Date of Patent: Dec. 11, 2018

(54) COMPOSITIONS FOR THE TREATMENT OF SWEATING AND METHODS FOR MAKING SAME

(71) Applicants: Clutch, Inc., Durham, NC (US); David Bradley Spratte, Jr., Decatur, GA (US); Christopher Jenks, Ames, IA (US); Kasper Kubica, South Ogden, UT (US); Mary Claire Brehm, Charlotte, NC (US); Shari Deanna Angelina Fonte Clemente, San Francisco, CA (US)

(72) Inventors: David Bradley Spratte, Jr., Decatur, GA (US); Christopher Jenks, Ames, IA (US); Kasper Kubica, South Ogden, UT (US); Mary Claire Brehm, Charlotte, NC (US); Shari Deanna Angelina Fonte Clemente, Cary, NC (US)

(73) Assignee: CLUTCH, INC., Durham, NC (US)

( * ) Notice: Subject to any disclaimer, the term of this patent is extended or adjusted under 35 U.S.C. 154(b) by 0 days.

(21) Appl. No.: 15/439,023

(22) Filed: Feb. 22, 2017

(65) Prior Publication Data
US 2017/0157006 A1 Jun. 8, 2017

Related U.S. Application Data

(63) Continuation-in-part of application No. 15/266,727, filed on Sep. 15, 2016.

(60) Provisional application No. 62/219,202, filed on Sep. 16, 2015.

(51) Int. Cl.
| | | |
|---|---|---|
| *A61K 8/26* | (2006.01) | |
| *A61Q 15/00* | (2006.01) | |
| *A61K 8/34* | (2006.01) | |
| *A61K 8/73* | (2006.01) | |
| *A61K 8/37* | (2006.01) | |
| *A61K 8/92* | (2006.01) | |
| *A61K 8/891* | (2006.01) | |
| *A61K 8/39* | (2006.01) | |
| *A61K 33/08* | (2006.01) | |

(52) U.S. Cl.
CPC ............ *A61K 8/26* (2013.01); *A61K 8/34* (2013.01); *A61K 8/37* (2013.01); *A61K 8/39* (2013.01); *A61K 8/731* (2013.01); *A61K 8/891* (2013.01); *A61K 8/922* (2013.01); *A61K 33/08* (2013.01); *A61Q 15/00* (2013.01)

(58) Field of Classification Search
CPC ............ A61K 8/26; A61K 33/08; A61Q 15/00
See application file for complete search history.

(56) References Cited

U.S. PATENT DOCUMENTS

| | | |
|---|---|---|
| 5,019,375 A | 5/1991 | Tanner et al. |
| 8,119,109 B2 | 2/2012 | Tamarkin et al. |
| 2003/0044469 A1* | 3/2003 | Viladot Petit ............ A61K 8/11 424/490 |
| 2007/0253911 A1 | 11/2007 | Tamarkin et al. |
| 2015/0050227 A1* | 2/2015 | Liu ........................ A61K 8/26 424/66 |
| 2015/0182424 A1* | 7/2015 | Schmit .................. A61K 8/046 424/47 |
| 2015/0196490 A1 | 7/2015 | Edelson et al. |

FOREIGN PATENT DOCUMENTS

| | | | | |
|---|---|---|---|---|
| EP | 0595339 A2 | * | 5/1994 | ............ A61K 8/046 |
| WO | 2006063114 A1 | | 6/2006 | |

OTHER PUBLICATIONS

Georgalas, A. "Antiperspirants and Deodorants" Cosmetics & Toiletries Feb. 2012, 127 (2), 94-99 (Year: 2012).*
Innocenzi et al, "An open-label tolerability and efficacy study of an aluminum sesquichlorhydrate topical foam n axillary and palmar primary hyperhidrosis", Dermatologic Therapy, 2008, S27-S30, vol. 21, Blackwell Publishing, United States.
Pariser et al, "Topical Therapies in Hyperhidrosis Care", Dermatologic Clinics—Hyperhydrosis. Dermatol Clin 32 (2014) 485-490.
Reisfeld et al, "Evidence-Based Review of the Nonsurgical Management of Hyperhidrosis", Thoracic Surgery Clinics, Journal of Thoracic Surgery, 2008, p. 157-166, vol. 18, Elsevier, United States.
Baumgartner et al, "Superiority of Thoracoscopic Sympathectomy over Medical Management for the Palmoplantar Subset of Severe Hyperhidrosis", Annal of Vascular Surgery, 2008, p. 1-7, vol. 23, Elsevier, United States.
Smith, F., "Hyperhidrosis", Vascular Surgery—II, 2013, p. 251-255, vol. 31, Elsevier, United States.
Drealos, Z., "Antiperspirants ans the Hyperhidrosis Patient" Dermatologic Therapy, 2001, p. 220-224, vol. 14, Issue 3, Blackwell Science, United States.
Merck Manual Home Edition article entitled, "Excessive Sweating: Sweating Disorders" accessed on Sep. 8, 2016 at www.merckmanuals.com/home/print/sec18/ch206/ch206c.html.
Benohanian, A., "Antiperspirants and Deodorants", Clinics in Dermatology, 2001, p. 398-405, vol. 19, Elsevier, United States.

(Continued)

*Primary Examiner* — Andrew S Rosenthal
(74) *Attorney, Agent, or Firm* — ePatentManager.com; Guerry L. Grune

(57) ABSTRACT

The invention describes novel compositions and methods utilized for treating disorders and/or conditions associated with the epidermal and/or dermal level of the skin. Such disorders include hyperhidrosis, bromhidrosis, and chromhidrosis, One representative composition of the invention comprises; water, alcohol, aluminum sesquichlorohydrate, hydroxypropyl methyl cellulose, polysorbate 20, isopropyl myristate, eucalyptus oil, silicone oil, alkyl benzoate, glycerine, talc, a hydrophillic silica, a hydrophobic silica, phenoxyethanol and ethylhexyl glycerine.

11 Claims, No Drawings

(56) References Cited

OTHER PUBLICATIONS

Christoph, R, Schmidt, B, Steinberner U, Dilla, W, and Karinen, R. Glycerol. In: Ullmann's Encyclopedia of Industrial Chemistry. vol. 17. Wiley and Sons, Inc.; 2006:67-82.

Glycerol. https://en.wikipedia.org/wiki/Glycerol.

Toxicological Evaluation of Certain Food Additives. http://www.inchem.org/documents/jecfa/jecmono/v10je06.htm.

* cited by examiner

COMPOSITIONS FOR THE TREATMENT OF SWEATING AND METHODS FOR MAKING SAME

PRIORITY

This application is a continuation-in-part of and claims priority under 35 USC 120 from U.S. nonprovisional application Ser. No. 15/266,727 filed Sep. 15, 2016, which is a nonprovisional conversion of and claims priority under 35 USC 119 from Provisional Application 62/216,202 filed Sep. 16, 2016, both entitled "Compositions for the Treatment of Sweating and Methods for Making Same", the entire contents of which are hereby incorporated by reference.

INTRODUCTION

The physiological act of sweating serves as the body's natural coolant, protecting it from overheating. When subjected to temperature increases, stress, or exercise, the body excretes sweat, a fluid comprising mostly water along with minerals, lactate and urea, to cool the body by evaporation of the water. Human sweat glands disorders are common and can have a significant impact on the quality of life and on professional, social, and emotional burdens. It is of paramount importance to diagnose and treat them properly to ensure optimal patient care. Hyperhidrosis is a medical condition characterized by excessive sweating in the armpits, palms of the hands, soles of the feet, face, scalp, and/or torso. Hyperhidrosis involves sweating in excess of the amount required for normal body activity levels and exposure to various temperate climates. There are two basic types of hyperhidrosis—primary and secondary. For primary hyperhidrosis, the cause is unknown and excessive sweating is localized in the armpits, hands, face, and/or feet. Primary hyperhidrosis begins during childhood or early adolescence, worsens during puberty, and usually lasts over a person's lifetime. In secondary hyperhidrosis, which is less common than primary hyperhidrosis, excessive sweating is caused by various medical conditions and usually occurs over the entire body. Medical conditions that can cause secondary hyperhidrosis include hyperthyroidism, menopause, obesity, psychiatric disorders, and diabetes. Secondary hyperhidrosis may also be caused by use of medications. In people with excessive sweating or hyperhidrosis, this function is overactive and they experience extreme sweating, more than is usual or necessary. This disorder can be uncomfortable, it can cause significant embarrassment and it can be emotionally debilitating. Excess sweating can occur on the palms of the hands, soles of the feet, underarms, face, head, or a combination of these sites or other sites on the body. Excessive sweating can lead to further dermatological disorders and social stigma. It is estimated that approximately two percent of the population suffers from hyperhidrosis.

Bromhidrosis and chromhidrosis are rare disorders but are still equally disabling as hyperhidrosis. Bromhidrosis occurs secondary to excessive secretion from either apocrine or eccrine glands that become malodorous on bacterial breakdown. The condition is further aggravated by poor hygiene or underlying disorders promoting bacterial overgrowth, including diabetes, intertrigo, erythrasma, and obesity. Chromhidrosis is a rare dermatologic disorder characterized by secretion of colored sweat with a predilection for the axillary area and the face. Treatment is challenging in that the condition usually recurs after discontinuation of therapy and persists until the age-related regression of the sweat glands.

BACKGROUND

Numerous therapeutic options have been introduced with variable success. Novel methods with microwave-based and ultrasound devices have been developed and are being tested in comparison to the conventional approaches. All treatment options for hyperhidrosis require frequent monitoring by a dermatologist for evaluation of the therapeutic progress. Over the counter antiperspirants are typically for use only on the underarms and can be irritating or otherwise less than optimal or effective for normal sweating. They can be ineffective in treating hyperhidrosis. Higher strength antiperspirants prescribed for the hyperhidrosis can also cause significant irritation. Surgical sypathectomy can cause unwanted compensatory sweating in other regions of the body. Botulinum toxin injections are very painful when used for treating palmar hyperhidrosis. Conventional tap water iontophoretic devices like the above are less than optimal. They are inconvenient to use, and immobilize the patient during treatment. They are also require the use of relatively high electric currents, around 18 milliamps, and which may, depending on the design, be directed through major portions of the body remote from the treatment area, including passing through the heart. They are typically painful for the person undergoing treatment due to the high current. This is a particular problem in that treatment often requires several sessions per week over a period of weeks or months.

Conventional treatments for hyperhidrosis include the use of antiperspirants, aluminum chloride, botulinum toxin injections, surgical procedures such as extrathoracic sympathectomy and electrical stimulation via tap water iontophoresis. Iontophoretic devices for the treatment of hyperhidrosis are described in example U.S. Patent Appln. Publication No. 2004/0167461 to Nitzan et al. and U.S. Pat. No. 6,223,076 to Tapper. WO 2010/027792 discloses the treatment of hyperhidrosis using galvanic particulates. US 2009/0232746 discloses a base formulation system for antiperspirants comprising an amidomethicone, dimethicone gum, and silica.

Topical agents applied to the skin in the affected area are a known first course of treatment for hyperhidrosis. Topical applications include anticholinergic drugs, boric acid, tannic acid, resorcinol, potassium permanganate, formaldehyde, glutaraldehyde and methenamine. Antiperspirant actives currently used in the industry are Lewis acids. Typically, such antiperspirant actives are partially neutralized chloride salts of metal ions such as aluminum and zirconium.

U.S. Pat. No. 6,433,003 discloses methods for treating hyperhidrosis involving the topical administration of glycopyrrolate compounds to humans. U.S. Pat. Nos. 5,730,964 and 5,512,555 teach methods of treating sweat related conditions with compounds that are 5-alpha-reductase inhibitors, such as finasteride, epristeride and cholestan-3-one, alone or in combination with other active agents to treat conditions such as apocrine gland sweating, hyperhidrosis, and hydradenitis suppurativa. U.S. Pat. No. 4,885,282 describes a method for the treatment of skin suffering from hyperhidrosis, ichthyosis or wrinkling, comprising applying to the affected area of a compound selected from the group consisting of mono- and dicarboxylic acids having 4 to 18 carbon atoms, a mercapto derivative thereof, a salt thereof, and an ester thereof.

US Pat. Application No. 20050196414 describes a method of administering a botulinum toxin to a subject comprising topically applying to the skin or epithelium of the subject the botulinum toxin for prevention or reduction of symptoms associated with subjective or clinical hyperhidrosis. US Pat. App. No. 20040192754 teaches compounds that can ameliorate symptoms of idiopathic hyperhidrosis and associated conditions include 5-HT2C receptor antagonists (i.e., ketanserin, ritanserin, mianserin, mesulergine, cyproheptadine, fluoxetine, mirtazapine, olanzapine, and ziprasidone) as well as 5-HT2C receptor modulators (i.e., inverse agonists, partial agonists, and allosteric modulators).

SUMMARY

In one aspect, the present invention features a composition provides a combination of aluminum sesquichlorohydrate with both hydrophobic and hydrophilic silica(s) disposed and/or infused in a water and alcohol based solution and a method of making the same. The composition treats hyperhidrosis (excessive sweating), and comprises topically applying the composition to skin in need of treatment for this condition.

More specifically, the composition is an anti-sweating composition comprising; water, alcohol, aluminum sesquichlorohydrate, hydroxypropyl methyl cellulose, polysorbate 20, isopropyl myristate, eucalyptus oil, silicone oil, alkyl benzoate, glycerine, talc, a hydrophillic silica and a hydrophobic silica, phenoxyethanol and ethylhexyl glycerine.

The components of the composition may allow for ethylhexyl glycerine to be replaced with chlorphenesin and caprylyl glycol.

The composition of the present invention also may comprise an aluminum hydrate and/or an aluminum chlorohydrate other than or including aluminum sesquichlorohydrate.

One embodiment allows for the composition described to include only hydrophobic silica. Another embodiment allows for the composition described to include only hydrophilic silica.

In another embodiment, the hydrophilic silica is Aerosil 300® and the hydrophobic silica is Aerosil R812®.

In a further embodiment, the silicone oil is polydimethyl siloxane (PDMS).

In a still further embodiment the alcohol is 2-propanol, the alkyl benzoate is C12-C15 alkyl benzoate, and the glycerine is vegetable derived glycerine.

Additionally the present composition may consist essentially of the following weight percentages of each component; 37-39 percent water, 11-12 percent 2-propanol, 14-15 percent aluminum sesquichlorohydrate, 12-13 percent hydroxypropyl methylcellulose, 4-5 percent polysorbate 20, 0.5-1.0 percent isopropyl myristate, 0.5-2.0 percent eucalyptus oil, 0.5-1.5 percent poly dimethyl siloxane, 1.0-2.0 alkyl benzoate, 0.5-1.0 percent glycerine, 1.0-3.0 percent talc, 5.0-7.0 percent hydrophilic silica, 4.0-6.0 percent hydrophobic silica, and 0.5-1.0 percent of the combination of phenoxyethanol and ethylhexyl glycerine.

For this composition the ethylhexyl glycerine may be replaced with chlorphenesin and caprylyl glycol at between 0.5 and 1.0 percent.

In addition, this composition also may contain citric acid and/or acetic acid or other "weaker" acids. These substances can be added for pH adjustment or can be utilized to increase shelf life or to otherwise improve the properties of the final composition.

The composition of the present invention provides for any selection of the group consisting of: a lotion, a cream, a spray, a moisturizer, a balm, a paste, and a saline solution.

The composition of the present invention may also be used to improve the condition of the foot, including sweating of the feet and all conditions associated with the feet.

One method for making an anti-sweating composition is as follows;
(i) adding purified and/or deionized and/or distilled water to a vessel with the necessary amounts and concentrations of NaOH and/or HCl or other strong base or strong acid to raise or lower the pH of the water to 8.5 (±0.1);
(ii) adding hydroxypropyl cellulose powder to the vessel and stir a resulting solution until the powder is fully hydrolyzed;
(iii) lower pH of said solution to 7.0 (±0.1) using a 1N HCl solution and begin rapid mixing;
(iv) adding Polysorbate 20 as an emulsifier for stabilizing oils during mixing
(v) adding aluminum sesquichlorohydrate during mixing, thereby lowering pH of the solution
(vi) adding silicone oil during mixing and ensuring viscosity of the solution does not exceed 200 centipoise;
(vii) adding isopropyl myristate during mixing;
(viii) adding alkyl benzoate during mixing;
(ix) adding eucalyptus oil during mixing;
(x) adding glycerine during mixing;
(xi) adding talc during mixing;
(xii) adding hydrophobic silica slowly during mixing to avoid funing of fumed silica into the atmosphere;
(xiii) raising the mixing speed once full amount of the hydrophobic silica is added to the solution;
(xix) adding a combination of phenoxyethanol and ethylhexyl glycerine as a preservative;
(xx) adding hydrophilic silica in the same manner as steps (xii) and (xiii);
and;
completing the composition by mixing until the composition is a homogeneous cream-like consistency.

A method of using the composition is also provided for a subject and the administering of the disclosed composition to the skin of the subject.

DETAILED DESCRIPTION

It is believed that one skilled in the art can, based upon the description herein, utilize the present invention to its fullest extent. The following specific embodiments are merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definition of Terms

As used herein, a composition that is "substantially free" of an ingredient means the composition that has about 2% or less of that ingredient by weight based on the total weight of the composition. Preferably, a composition that is substantially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is substantially free of an ingredient is free of the ingredient, i.e. has none of that ingredient in the composition.

As used herein, "cosmetically-acceptable" means that the ingredients which the term describes are suitable for use in contact with tissues (e.g., the skin or hair) without undue toxicity, incompatibility, instability, irritation, allergic response, and the like.

As used herein, "safe and effective amount" means an amount of the ingredient or of the composition sufficient to provide the desired benefit at a desired level, but low enough to avoid serious side effects. The safe and effective amount of the ingredient or composition will vary with the area being treated, the age and skin type of the end user, the duration and nature of the treatment, the specific ingredient or composition employed, the particular cosmetically-acceptable topical carrier utilized, and like factors.

As used herein, the term "treatment" means the alleviation or elimination of symptoms, and/or cure, and/or prevention or inhibition of a disease or condition, specifically sweating.

As used herein, "sweating" refers to the excretion of perspiration from the pores of the skin. Sweating includes, but not limited to, 1) non-pathological sweating, such as thermally-induced, exercise-induced, or stress-induced sweating; and 2) pathological or excessive sweating such as hyperhidrosis, including primary and secondary hyperhidrosis, as well as focal and generalized hyperhidrosis. The invention is useful in any area of the body where sweating occurs such as the hands, feet, face, head, torso, or under-arms (axilla).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (e.g., any disease, disorder, or condition, including, but not limited to, any disease, disorder, or condition described herein) has been diagnosed with or exhibits symptoms of the disease, disorder, or condition. In some embodiments, exemplary diseases, disorders, or conditions include, but are not limited to, a condition associated with sweat glands or sebaceous glands, such as acne; hyperhidrosis; unwanted sweating; bromhidrosis; body odor; chromhidrosis; hair loss; psoriasis; actinic keratosis; dermal infection; eczematous dermatitis (e.g., atopic dermatitis, etc.); excess sebum-producing disorder; burns; Raynaud's phenomenon; lupus erthythematosus; hyperpigmentation disorder, hypopigmentation disorder; skin cancer; etc.

Susceptible to: An individual who is "susceptible to" a disease, disorder, or condition (e.g., any disease, disorder, or condition, including, but not limited to, any disease, disorder, or condition described herein) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to an infectious agent; the individual has been exposed to an environmental hazard thought to cause the disease, disorder, and/or condition; etc.). In some embodiments, a risk of developing a disease, disorder, and/or condition is a population-based risk (e.g., an individual carries a gene and/or allele associated with the disease, disorder, and/or condition).

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. To give but a few examples, where the condition in question is acne, symptoms of that condition are reduced when the (e.g., diameter, volume, etc.) and/or severity (e.g., redness, inflammatory response, etc.) of one or more blemishes in the selected area is reduced, and/or when the number of total blemishes is reduced (e.g., on a subject's face, back, etc.). Where the condition in question is hyperhidrosis and/or unwanted sweating, symptoms are reduced when the subject produces less sweat. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutically effective amount: As used herein, the term "therapeutically effective amount" means an amount that is sufficient, when administered to a population suffering from or susceptible to a disease, disorder, and/or condition, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues. Those of ordinary skill in the art will appreciate that, in some embodiments, a therapeutically effective agent may be formulated and/or administered in a single dose. In some embodiments, a therapeutically effective agent may be formulated and/or administered in a plurality of doses, for example, as part of a dosing regimen.

Therapeutic agent: As used herein, the phrase "therapeutic agent" refers to any agent that has a therapeutic effect and/or elicits a desired biological and/or pharmacological effect, when administered to a subject. Exemplary therapeutic agents include but are not limited to botulinum toxins and monoclonal antibodies and fragments thereof.

Toxic solvent: As used herein, the term "toxic solvent" refers to any substance that may alter, disrupt, remove, or destroy an animal's tissue. As would be understood by one of ordinary skill in the art, an animal's tissue can include living cells, dead cells, extracellular matrix, cellular junctions, biological molecules, etc. To give but a few examples, toxic solvents include dimethyl sulfoxide, dimethyl acetimide, dimethyl formamide, chloroform, tetramethyl formamide, acetone, acetates, and alkanes.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unwanted side effects: As used herein, the term "unwanted side effects" refers to one or more effects and/or symptoms associated with administration of a substance to a patient that are not the desired and/or intended effects and/or are unpleasant to the patient. Exemplary unwanted side effects include pain; bruising; ecchymosis; hematoma; botulism poisoning; unwanted systemic effects; undesirable blood levels of the administered substance; damage to underlying nervous tissue (e.g., neuronal paralysis); unwanted effects on muscles (e.g., muscle paralysis); flu-like symptoms; morbidity; mortality; alteration in body weight; alteration in enzyme levels; pathological changes detected at the microscopic, macroscopic, and/or physiological levels; infection; hemorrhage; inflammation; scarring; loss of function; changes in local blood flow; fever; malaise; teratogenesis; pulmonary hypertension; stroke; heart disease; heart attack; neuropathy; nausea; vomiting; dizziness; diarrhea; headache; dermatitis; dry mouth; addiction; miscarriage; abortion; uterine hemorrhage; birth defects; bleeding; cardiovascular disease; deafness; kidney damage and/or failure; liver damage and/or failure; dementia; depression; diabetes; erectile dysfunction; glaucoma; hair loss; anaemia; insomnia; lactic acidosis; melasma; thrombosis; priapism; rhabdomyolysis; seizures; drowsiness; increase in appetite; decrease in appetite; increase in libido; decrease in libido; tardive dyskinesia; non-axillary sweating; injection site pain and hemorrhage; pharyngitis; neck pain; back pain; pruritus; anxiety; follicular obstruction; and/or combinations thereof. In some embodiments, topical administration of a provided compositions reduce unwanted side effects by about 50%, about 60%, about 70%, about 80%, about 90%, about 95%, about 98%, about 99%, or about 100% relative to non-topical administration (e.g., injection, oral administration, etc.) of the same substance.

Detailed Description of the Composition

In one embodiment, the composition comprises a combination of aluminum sesquichlorohydrate with both hydrophobic and hydrophilic silica(s) disposed and/or infused in a water and alcohol base. Further, the composition comprises at least one silicone oil. One additional example of a suitable silicone oil compositions in addition to the use of dimethicone (PDMS—Polydimethylsiloxane), includes a blend comprising; cyclopentasiloxane, dimethicone, dimethicone crosspolymer, trisiloxane, silica, and dimethicone/vinyl dimethicone crosspolymer. Such a blend is commercially available as DOW CORNING® CF-0055 Custom Blend.

The composition is preferably applied in a safe and effective amount for the treatment of sweating. For example, the amount of a composition comprising a silicone applied to the palm of the hand is preferably about one-half the size of a pea. This amount may be applied several times during the day, for example once in the morning, then throughout the day after each washing the hands or other removal of the composition, and then again at bedtime. Alternatively, the composition may be applied twice a day, in the morning and at bedtime, or applied once a day at bedtime.

In a primary embodiment, the use of aluminum sesquichlorohydrate is used as the primary active ingredient that either eliminates, prevents, or at least reduces excessive sweating or hyperhidrosis. A recent investigation by Innocenzi, et. al., entitled "An Open-Label Tolerability and Efficacy Study of an Aluminum Sesquichlorohydrate Topical Foam in Axillary and Palmar Primary Hyperhidrosis", published in *Dermatol Ther.* 2008 July; 21 Suppl 1:S27-30. doi: 10.1111/j.1529-8019.2008.00199 indicated that the aluminum sesquichlorohydrate foam indicated a significant reduction of eccrine sweating (61%) with only a single patient (out of 20) reporting any type of skin irritation.

The composition may be applied to the treatment area in a variety of forms including but not limited to gels, creams, or sticks. In one embodiment, the composition comprises a cosmetically-acceptable topical carrier.

As will be recognized by those of skill in the art, cosmetically-acceptable topical carriers comprise carriers that are suitable for use in contact with the body, in particular the skin for treatment of sweating, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 99.8% to about 98% of the composition. The carrier can take a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps. Examples of suitable cosmetically-acceptable topical carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, make-up, liquid drops, and the like. These product types may contain several types of cosmetically-acceptable topical carriers including, but not limited to solutions, suspensions, emulsions such as microemulsions and gels, solids, liposomes, other encapsulation technologies and the like. The following are non-limitative examples of such carriers. Other carriers can be formulated by those of ordinary skill in the art.

In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols. Examples of glycols include, but are not limited to, glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99%.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water.

An alternative that may be used as a substitute for Euxyl PE9010 is Mikrokill® COS, which is a unique, patented combination of three components (Phenoxyethanol, Chlorphenesin and Caprylyl Glycol) manufactured by Lonza and which are also antibacterial compositions that can be interchangeably used with the composition presented in Table 1 above.

Another type of product that may be formulated from the compositional solution provided in Table 1 is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from the compositional solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid or dissolvable substrate (e.g., a wipe, mask, pad, glove or strip).

The composition is applied topically by simple rubbing with the fingers, spraying, or with other applicators known in the art of topical compositions, such as, but not limited to, a pad or wipe.

In one embodiment, the composition contacts substantially all, that is, at least 80 percent, preferably 90 percent, of the surface area of the skin in need of treatment. More preferably, the composition contacts all, that is, 100 percent, of the surface area of the skin in need of treatment.

In an additional embodiment, the composition contains one or more other ingredients typically used in topical compositions, many of which are familiar to those skilled in the art. For example, the composition may contain plant extracts, anti-inflammatory agents, antimicrobial agents, fragrances, or other active agents used to treat sweating.

Examples of plant extracts include, but are not limited to, feverfew, soy, glycine soja, oatmeal, what, aloe vera, cranberry, witch-hazel, alnus, arnica, artemisia capillaris, asiasarum root, birch, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata, natural isoflavonoids, soy isoflavones, and natural essential oils.

In another embodiment, the composition contains ingredients to alleviate or prevent skin irritation and inflammation. These ingredients may include natural extracts, such as but not limited to feverfew, aloe, or chamomile. In another embodiment these ingredients may include topical steroids including corticosteroids, such as hydrocortisone. In yet another embodiment, the composition may include nonsteroidal anti-inflammatory agents.

The composition of the present invention may also include a buffering agent such as citrate buffer, phosphate buffer, lactate buffer, gluconate buffer, or gelling agents, thickeners, or polymers. The use of a fragrance, for example one effective for reducing stress, calming, and/or affecting sleep such as lavender and chamomile may also be employed.

The following non-limiting example in Table 1 further illustrates the invention.

TABLE 1

Example 1: Composition for Treating Hyperhidrosis

| Constituent | Weight (grams) | Weight % |
|---|---|---|
| Water | 23.0 | 38.9 |
| 2-propanol (100%) | 7.0 | 11.8 |
| Aluminum Sesquichlorohydrate (active) | 8.8 | 14.9 |
| Methocel ® 40-0101 3% (Hydroxypropyl Methylcellulose) | 7.5 | 12.7 |
| Polysorbate 20 (Polyoxyethylene -chain length of 20 units and sorbitan monolaurate) | 2.0 | 3.4 |
| Isopropyl Myristate | 0.5 | 0.8 |
| Eucalyptus Oil | 0.5 | 0.8 |
| Dimethicone (- PDMS - Polydimethylsiloxane) | 0.8 | 1.4 |
| Alkyl Benzoate | 1.0 | 1.7 |
| Glycerin | 0.5 | 0.8 |
| Talc | 1.0 | 1.7 |
| *Aerosil 300 (hydrophilic) | 3.0 | 5.1 |
| **Aerosil R812 (hydrophobic) | 3.0 | 5.1 |
| ***Euxyl PE9010 | 0.5 | 0.8 |
| TOTAL: | 59.1 | 100.0 |

*AEROSIL ® 300 is a hydrophilic fumed silica with a specific surface area of 300 m²/g, manufactured by Evonik Industries of Germany
**AEROSIL ® R 812 S is a fumed silica "aftertreated" with HMDS (hexamethyl disiloxane) also manufactured by Evonik of Germany
***Euxyl PE9010 (a liquid cosmetic composition containing phenoxyethanol and ethylhexyl glycerine) and is manufactured by Schulke of Germany.

TABLE 2

Example 2: Composition for Treating Hyperhidrosis

| Constituent | Weight % |
|---|---|
| Water | 37.5 |
| 2-propanol (100%) | 11.1 |
| Aluminum Sesquichlorohydrate (active) | 14.4 |
| Methocel ® 40-0101 3% (Hydroxypropyl Methylcellulose) | 12.2 |
| Polysorbate 20 (Polyoxyethylene -chain length of 20 units and sorbitan monolaurate) | 4.9 |
| Isopropyl Myristate | 0.8 |
| Eucalyptus Oil | 1.6 |
| Dimethicone (- PDMS - Polydimethylsiloxane) | 0.8 |
| Alkyl Benzoate | 1.6 |
| Glycerin | 0.8 |
| Talc | 2.4 |
| *Aerosil 300 (hydrophilic) | 6.5 |
| **Aerosil R812 (hydrophobic) | 4.1 |
| ***Mikrokill ® COS | 0.8 |
| TOTAL: | 100.0 |

*AEROSIL ® 300 is a hydropbilic fumed, silica with a specific surface area of 300 m²/g, manufactured by Evonik Industries of Germany
**AEROSIL ® R 812 S is a fumed silica "aftertreated" with HMDS (hexamethyl disiloxane) also manufactured by Evonik of Germany
***Mikrokili ® COS which is a unique, patented combination of three components (Phenoxyethanol, Chlorphenesin and Caprylyl Glycol) manufactured by Lonza of Germany In some embodiments, a cream and/or lotion formulation comprises and/or consists essentially of the following proportions of ingredients:

TABLE 3

Example 3: Anti-Hyperhidrosis Cream and/or Lotion

| Constituent | Weight % |
|---|---|
| Purified Water | 40% |
| Alcohol | 12% |
| Aluminum Sesquichlorohydrate (active) | 15% |
| White Petrolatum | 2.0% |
| Isopropyl Myristate | 4.0% |
| Mineral Oil | 1.9% |
| Dimethicone (-PDMS-Polydimethylsiloxane) | 1.4% |
| Alkyl Benzoate | 1.7% |
| Glycerin | 1.0% |
| Emulsifying Wax | 10.0% |
| *Aerosil 300 (hydrophilic) | 5.0% |
| **Aerosil R812 (hydrophobic) | 5.0% |
| ***Euxyl PE9010 | 1.0% |
| TOTAL: | 100.0 |

In some embodiments, a saline solution for bulk formulation comprises and/or consists essentially of the components found in Table 4 below;

TABLE 4

Example 4: Anti-Hyperhidrosis Saline Solution

| Constituent | Weight % |
|---|---|
| Isotonic Sodium Chloride Solution | 65% |
| Alcohol | 10% |
| Aluminum Sesquichlorohydrate (active) | 15% |
| Glycerin | 1.0% |
| Emulsifying Wax | 3.0% |
| ***Euxyl PE9010 | 1.0% |
| TOTAL: | 100.0 |

The present invention encompasses the recognition that provided cream and/or lotion formulations can be particularly useful for topical and/or transdermal administration. The present invention encompasses the recognition that provided cream and/or lotion formulations can be particularly useful for delivery of agents to the dermal level of the skin. In some embodiments, provided cream and/or lotion formulations are formulated for topical and/or transdermal delivery to a subject in need thereof. In some embodiments, provided cream and/or lotion formulations are administered to a subject in need thereof via topical and/or transdermal delivery.

In further embodiments, provided cream and/or lotion formulations comprise purified water, methylparaben, mineral oil, isopropyl myristate, white petrolatum, emulsifying wax, and propylparaben. In some embodiments, provided cream and/or lotion formulations comprise purified water, mineral oil, isopropyl myristate, white petrolatum, and emulsifying wax. In some embodiments, provided cream and/or lotion formulations comprise the components set forth in Table 1.

In some embodiments, the present invention provides particular cream and/or lotion formulations as described herein. In some embodiments, provided cream and/or lotion formulations comprise water. In some embodiments, provided cream and/or lotion formulations comprise methylparaben. In some embodiments, provided cream and/or lotion formulations comprise mineral oil. In some embodiments, provided cream and/or lotion formulations comprise isopropyl myristate. In some embodiments, provided cream and/or lotion formulations comprise white petrolatum. In some embodiments, provided cream and/or lotion formulations comprise emulsifying wax. In some embodiments, provided cream and/or lotion formulations comprise propylparaben. In some embodiments, provided cream and/or lotion formulations do not comprise any parabens. In some embodiments, provided cream and/or lotion formulations do not comprise methylparaben. In some embodiments, provided cream and/or lotion formulations do not comprise propylparaben.

The present invention encompasses the recognition that cream and/or lotion formulations can be particularly useful for formulating compositions, such as those described herein, for administration to a subject.

The present invention provides that surprising and/or unexpected results can be achieved when cream and/or lotion formulations are formulated specifically with aluminum sesquichlorohydrate as an active substance in a water and alcohol base.

In some embodiments, compositions comprise a mixture of one or more pharmaceutically acceptable excipients. In some embodiments, these compositions separately or together comprise a mixture of a saline solution, and a cream and/or lotion formulation, as described herein.

In some embodiments, the present invention provides methods of treating any mammalian skin conditions or disorders. In some embodiments, the present invention demonstrates that certain compositions as described herein can achieve controlled delivery of active agents efficiently and specifically to biologically relevant target sites (e.g., particular tissues, locations within the skin, cells, etc.). In some embodiments, the present invention demonstrates controlled delivery and/or achievement of a therapeutic effect in a certain biologically relevant target site without significant side effects associated with delivery to other areas.

In some embodiments, the present invention provides methods of treating conditions or disorders associated with epidermal and/or dermal structures (e.g., sweat glands, sebaceous glands, hair follicles, etc.). In some embodiments, the present invention demonstrates that provided compositions as described herein can deliver active agents efficiently and specifically to the dermis, and that provided compositions as described herein can have therapeutic effects upon administration to the skin of a subject. In some embodiments, the present invention demonstrates dermal delivery and/or achievement of therapeutic effect without significant side effects associated with delivery to other areas (e.g., to subdermal or extradermal structures and/or to tissues other than dermis). In some embodiments, provided compositions may be formulated and/or delivered so that systemic delivery is achieved; in some embodiments, provided compositions may be formulated and/or delivered so that local, but not systemic, delivery is achieved.

This application refers to various patent and non-patent publications, all of which are incorporated herein by reference.

Those of ordinary skill in the art will also be well aware of suitable oily media that can be used as dispersion media or as media to be dispersed in accordance with the present invention. In some embodiments, oils may comprise one or more fatty acid groups or salts thereof. In some embodiments, a fatty acid group may comprise digestible, substituted or unsubstituted hydrocarbons. In some embodiments, a fatty acid group may be a $C_6$-$C_{50}$ fatty acid or salt thereof.

In some embodiments, a fatty acid group may be a $C_6$-$C_{20}$ fatty acid or salt thereof. In some embodiments, a fatty acid group may be a $C_6$-$C_{16}$ fatty acid or salt thereof. In some embodiments, a fatty acid group may be a $C_6$-$C_{12}$ fatty acid or salt thereof. In some embodiments, a fatty acid group may be a $C_6$ fatty acid or salt thereof. In some embodiments, a fatty acid group may be a $C_8$ fatty acid or salt thereof. In some embodiments, a fatty acid group may be a $C_{10}$ fatty acid or salt thereof. In some embodiments, a fatty acid group may be a $C_{12}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation. In some embodiments, a fatty acid group may be one or more of butyric, caproic, caprylic, capric, lauric, myristic, palmitic, stearic, arachidic, behenic, lignoceric acid, and/or combinations thereof. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, erucic acid, and/or combinations thereof.

In some embodiments, the comprises an oily dispersion medium that comprises, consists essentially of, or consists of a medium chain triglyceride (e.g., fatty acids containing 6-12 carbons atoms, such as caprylic acid, octanoic acid, capric acid, decanoic acid, lauric acid, etc., which, in some embodiments, may be obtained from coconut oil or palm kernel oil). Exemplary medium chain triglycerides include monounsaturated, and/or polyunsaturated soybean oil, coconut oil, canola oil, safflower oil, olive oil, corn oil, cottonseed oil, linseed oil, safflower oil, palm oil, peanut oil, flaxseed oil, sunflower oil, rice bran oil, sesame oil, rapeseed oil, cocoa butter, almond oil, cashew oil, hazelnut oil, mongongo nut oil, acai oil, borage seed oil, evening primrose oil, carob pod oil, amaranth oil, apple seed oil, artichoke oil, avocado oil, babassu oil, ben oil, borneo tallow nut oil, cocoa butter, cocklebur oil, cohune oil, dika oil, grape seed oil, hemp oil, kapok seed oil, kenaf seed oil, lallemantia oil, marula oil, meadowfoam seed oil, mustard oil, papaya seed oil, perilla seed oil, pequi oil, poppyseed oil, prune kernel oil, quinoa oil, tea seed oil, thistle oil, tigernut oil, tomato seed oil, wheat germ oil, Labrafac™ Lipophile WL 1349 oil, a silicone oil, a mineral oil, a lauroyl macrogol-6 glyceride, a lauroyl polyoxyl-6 glyceride, an oleoyl macrogol-6 glyceride, an oleoyl polyoxyl-6 glyceride, a linoleoyl macrogol-6 glyceride, a linoleoyl polyoxyl-6 glyceride, propylene glycol monocaprylate, propylene glycol monolaurate, propylene glycol monolaurate, polglyceryl-3 dioleate, propylene glycol dicaprylocaprate, diethylene glycol monethyl ether, a caprylocaproyl macrogol-8 glyceride, a caprylocaproyl polyoxyl-8 glyceride, and/or combinations thereof.

In some embodiments, an oil is or comprises saturated, monounsaturated, and/or polyunsaturated short-chain fatty acids, medium-chain fatty acids, long-chain fatty acids, very-long-chain fatty acids, and/or combinations thereof. In some embodiments, exemplary very-long-chain fatty acids include, but are not limited to, myristoleic acid, palmitoleic acid, sapienic acid, oleic acid, linoleic acid, alpha linolenic acid, arachidonic acid, eicosapentaenoic acid, erucic acid, docoshexaenoic acid, lauric acid, myristic acid, palmitic acid, stearic acid, arachidic acid, behenic acid, lignoceric acid, cerotic acid, and/or combinations thereof.

In some embodiments, an oil is selected from the group consisting of short-chain triglycerides, medium-chain triglycerides, long-chain triglycerides, and/or combinations thereof. In some embodiments, a short-chain triglyceride, a medium-chain triglyceride, and/or a long-chain triglyceride selected from the group consisting of saturated, monounsaturated, and/or polyunsaturated soybean oil, coconut oil, canola oil, safflower oil, olive oil, corn oil, cottonseed oil, linseed oil, safflower oil, palm oil, peanut oil, flaxseed oil, sunflower oil, rice bran oil, sesame oil, rapeseed oil, cocoa butter, almond oil, cashew oil, hazelnut oil, macadamia oil, mongongo nut oil, pecan oil, pine nut oil, pistachio oil, sachainchi oil, walnut oil, bottle gourd oil, buffalo gourd oil, butternut squash seed oil, pumpkin seed oil, watermelon seed oil, acai oil, blackcurrant seed oil, borage seed oil, evening primrose oil, carob pod oil, amaranth oil, apricot oil, apricot kernel oil, apple seed oil, argan oil, artichoke oil, avocado oil, babassu oil, ben oil, borneo tallow nut oil, cape chestnut oil, cassia oil, cocoa butter, cocklebur oil, cohune oil, coriander seed oil, dika oil, grape seed oil, hemp oil, kapok seed oil, kenaf seed oil, lallemantia oil, marula oil, meadowfoam seed oil, mustard oil, nutmeg butter, okra seed oil, papaya seed oil, perilla seed oil, pequi oil, poppyseed oil, prune kernel oil, quinoa oil, ramtil oil, royle oil, tea seed oil, thistle oil, tigernut oil, tomato seed oil, wheat germ oil, radish oil, salicornia oil, tung oil, algae oil, copaiba oil, honge oil, jatropha oil, petroleum nut oil, WL 1349 oil, a silicone oil, a mineral oil, a lauroyl macrogol-6 glyceride, a lauroyl polyoxyl-6 glyceride, an oleoyl macrogol-6 glyceride, an oleoyl polyoxyl-6 glyceride, a linoleoyl macrogol-6 glyceride, a linoleoyl polyoxyl-6 glyceride, propylene glycol monocaprylate, propylene glycol monolaurate, propylene glycol monolaurate, polglyceryl-3 dioleate, propylene glycol dicaprylocaprate, diethylene glycol monethyl ether, a caprylocaproyl macrogol-8 glyceride, a caprylocaproyl polyoxyl-8 glyceride, and/or combinations thereof.

In other some embodiments, an oil agent is or comprises saturated, monounsaturated, and/or polyunsaturated soybean oil, coconut oil, canola oil, safflower oil, olive oil, corn oil, cottonseed oil, linseed oil, safflower oil, palm oil, peanut oil, flaxseed oil, sunflower oil, rice bran oil, sesame oil, rapeseed oil, cocoa butter, almond oil, cashew oil, hazelnut oil, macadamia oil, mongongo nut oil, pecan oil, pine nut oil, pistachio oil, sachainchi oil, walnut oil, bottle gourd oil, buffalo gourd oil, butternut squash seed oil, pumpkin seed oil, watermelon seed oil, acai oil, blackcurrant seed oil, borage seed oil, evening primrose oil, carob pod oil, amaranth oil, apricot oil, apricot kernel oil, apple seed oil, argan oil, artichoke oil, avocado oil, babassu oil, ben oil, borneo tallow nut oil, cape chestnut oil, cassia oil, cocoa butter, cocklebur oil, cohune oil, coriander seed oil, dika oil, grape seed oil, hemp oil, kapok seed oil, kenaf seed oil, lallemantia oil, manila oil, meadowfoam seed oil, mustard oil, nutmeg butter, okra seed oil, papaya seed oil, perilla seed oil, pequi oil, poppyseed oil, prune kernel oil, quinoa oil, ramtil oil, royle oil, tea seed oil, thistle oil, tigernut oil, tomato seed oil, wheat germ oil, radish oil, salicornia oil, tung oil, algae oil, copaiba oil, honge oil, jatropha oil, petroleum nut oil, WL 1349 oil, a silicone oil, a mineral oil, a lauroyl macrogol-6 glyceride, a lauroyl polyoxyl-6 glyceride, an oleoyl macrogol-6 glyceride, an oleoyl polyoxyl-6 glyceride, a linoleoyl macrogol-6 glyceride, a linoleoyl polyoxyl-6 glyceride, propylene glycol monocaprylate, propylene glycol monolaurate, propylene glycol monolaurate, polglyceryl-3 dioleate, propylene glycol dicaprylocaprate, diethylene glycol monethyl ether, a caprylocaproyl macrogol-8 glyceride, a caprylocaproyl polyoxyl-8 glyceride, bergamot, cade, camomile, caraway, carnauba, castor, cinnamon, cod liver, coffee, emu, eucalyptus, fish, geraniol, hyssop, jojoba, kukui nut, lavandin, lavender, lemon, litsea cubeba, mallow, mango seed, mink, orange, orange roughy, palm kernel, peach kernel, rosemary, sandalwood, sasquana, savoury, sea buckthorn, shea butter, tea tree, tsubaki, vetiver, butyl stearate, caprylic triglyceride, capric triglyceride, cyclomethicone, diethyl sebacate, dimethicone 360, isopropyl myristate, octyldodecanol, oleyl alcohol, and/or combinations thereof.

Suitable surfactants or emulsifying agents include, but are not limited to, pemulen; phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester, diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides: sorbitan trioleate (SPAN®85) glycocholate; sorbitan monolaurate (SPAN®20); polyoxyethylene monostearate; surfactin; a poloxomer: a sorbitan fatty acid ester such as sorbitan trioleate; lecithin; lysolecithin; phosphatidylserine; phosphatidylinositol; sphingomyelin; phosphatidylethanolamine (cephalin): cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine: poly(ethylene glycol)400-monostearate; phospholipids; synthetic and/or natural detergents having high surfactant properties; deoxycholates; cyclodextrins; chaotropic salts; ion pairing agents; sodium dodecyl sulfate; pemulen; an amphiphilic entity having a head group based on a polyoxyethylene glycol sorbitan alkyl ester (e.g., as in a polysorbate (TWEEN®), a super-refined polysorbate (TWEEN®, and/or combination thereof; including, but not limited to, polysorbate 20 (TWEEN®20); polysorbate 60 (TWEEN®60); polysorbate 65 (TWEEN®65); polysorbate 80 (TWEEN®80); polysorbate 85 (TWEEN®85); super-refined polysorbate 20 (SR TWEEN®20): super-refined polysorbate 60 (SR TWEEN®60); super-refined polysorbate 65 (SR TWEEN®65) super-refined polysorbate 80 (SR TWEEN®80); super-refined polysorbate 85 (SR TWEEN®85); and/or combinations thereof); an amphiphilic entity having a sulfate-based head group (e.g., as in ammonium lauryl sulfate, sodium lauryl sulfate, sodium laureth sulfate, sodium myreth sulfate, etc.); an amphiphilic entity having a sulfonate-based head group (e.g., as in dioctyl sodium sulfosuccinate, perfluorooctanesulfonate [PFOS], perfluorobutanesulfonate, alkyl benzene sulfonates, CHAPS (3-[(3-Cholamidopropyl)dimethylammonio]-1-propanesulfonate, cocamidopropyl hydroxysultaine, etc.); an amphiphilic entity having a phosphate-based head group (e.g., as in alkyl aryl ether phosphate, alkyl ether phosphate, lecithin, etc.); an amphiphilic entity having a carboxylate-based head group (e.g., as in fatty acids, sodium stearate, sodium lauroyl sarcosinate, carboxylate fluorosurfactants, perfluorononanoate, perfluorooctanoate [PFOA or PFO], amino acids, imino acids, cocamidopropyl betaine, etc.); an amphiphilic entity having an amine-based head group (e.g., a primary, secondary, or tertiary amine, as in octenideine dihydrochloride); an amphiphilic entity having a head group comprising a quaternary ammonium ion (e.g., as in cetyl trimethylammonium bromide [CTAB] a.k.a. hexadecyl trimethyl ammonium bromide, cetyl trimethylammonium chloride [CTAC], cetylpyridinium chloride [CPC], polyethoxylated tallow amine [POEA], benzalkonium chloride [BAC], Benzethonium chloride [BZT], 5-Bromo-5-nitro-1,3-dioxane, Dimethyldioctadecylammonium chloride, Dioctadecyldimethylammonium bromide [DODAB]); an amphiphilic entity having a head group based on a fatty alcohol (e.g., as in cetyl alcohol, stearyl alcohol, cetostearyl alcohol, oleyl alcohol, etc.); an amphiphilic entity having a head group based on a polyoxyethylene glycol alkyl ether (e.g., as in octaethylene glycol monododecyl ether, pentacthylene glycol monododecyl ether); an amphiphilic entity having a head group based on polyoxypropylene glycol alkyl ether; an amphiphilic entity having a head group based on a glucoside alkyl ether (e.g., as in decyl glucoside, lauryl glucoside, octyl glucoside, etc.); an amphiphilic entity having a head group based on a polyoxyethylene glycol octylphenol ether (e.g., as in Triton X-100); an amphiphilic entity having a head group based on a polyoxyethylene glycol alkylphenol ether (e.g., as in nonosynol-9); an amphiphilic entity having a head group based on a glycerol alkyl ester (e.g., as in glyceryl laurate); an amphiphilic entity having a head group based on a sorbitan alkyl ester (e.g., spans); an amphiphilic entity that is or comprises cocamide MEA, cocamide DEA<dodecyl dimethylamine oxide; a block copolymer of polyethylene glycol and polypropylene glycol (i.e., a poloxamer); an amphiphilic entity having a tail group based on or containing a hydrocarbon chain: an amphiphilic entity having a tail group based on or containing an alkyl ether chain; an amphiphilic entity having a tail group based on or containing a polyethylene; an amphiphilic entity having a tail group based on or containing polypropylene oxide; an amphiphilic entity having a tail group based on or containing a fluorocarbon chain; an amphiphilic entity having a tail group based on or containing a siloxane chain; and/or combinations thereof.

In some embodiments, a surfactant is a mixture of different surfactants. Surfactants may be extracted and purified from a natural source or may be prepared synthetically in a laboratory. In some embodiments, surfactants are commercially available.

Gels may also be employed and one of ordinary skill in the art would readily appreciate that gelatin itself may not be the only agent with desirable attributes, such as those described herein, and could readily test a variety of agents, particularly peptide agents, to identify additional agents having similar attributes and/or functions. Exemplary peptide agents that could be tested for attributes and/or functions similar to those exhibited by gelatin include, but are not limited to, proteins derived from blood and/or plasma, including, but not limited to, albumin, fibrin, thrombin, prothrombin, and/or combinations thereof.

In some embodiments, the present invention provides compositions comprising one or more of a medium chain triglyceride, a polysorbate, and gelatin.

In some embodiments, oil and surfactant are utilized at a ratio ranging between 0.1 and 2. In some embodiments, the ratio of oil to surfactant is approximately 0.1:1. In some embodiments, the ratio of oil to surfactant is approximately 0.15:1. In some embodiments, the ratio of oil to surfactant is approximately 0.2:1. In some embodiments, the ratio of oil to surfactant is approximately 0.25:1. In some embodiments, the ratio of oil to surfactant is approximately 0.3:1. In some embodiments, the ratio of oil to surfactant is approximately 0.35:1. In some embodiments, the ratio of oil to surfactant is approximately 0.4:1. In some embodiments, the ratio of oil to surfactant is approximately 0.45:1. In some embodiments, the ratio of oil to surfactant is approximately 0.5:1. In some embodiments, the ratio of oil to surfactant is approximately 0.55:1. In some embodiments, the ratio of oil to surfactant is approximately 0.6:1. In some embodiments, the ratio of oil to surfactant is approximately 0.65:1. In some embodiments, the ratio of oil to surfactant is approximately 0.7:1. In some embodiments, the ratio of oil to surfactant is approximately 0.75:1. In some embodiments, the ratio of oil to surfactant is approximately 0.8:1. In some embodiments, the ratio of oil to surfactant is approximately 0.85:1. In some embodiments, the ratio of oil to surfactant is approximately 0.9:1. In some embodiments, the ratio of oil to surfactant is approximately 0.95:1. In some embodiments, the ratio of oil to surfactant is approximately 1:1. In some embodiments, the ratio of oil to surfactant is approximately 1:1.05. In some embodiments, the ratio of oil to surfactant is approximately 1:1.1. In some embodiments, the ratio of oil to surfactant is approximately 1:1.15. In some embodiments, the ratio of oil to surfactant is approximately 1:1.2. In some embodiments, the ratio of oil to surfactant is approximately 1:1.25. In some embodiments, the ratio of oil to surfactant is approximately 1:1.3. In some embodiments, the ratio of oil to surfactant is approximately 1:1.35. In some embodiments, the ratio of oil to surfactant is approximately 1:1.4. In some embodiments, the ratio of oil to surfactant is approximately 1:1.45. In some embodiments, the ratio of oil to surfactant is approximately 1:1.5. In some embodiments, the ratio of oil to surfactant is approximately 1:1.55. In some embodiments, the ratio of oil to surfactant is approximately 1:1.6. In some embodiments, the ratio of oil to surfactant is approximately 1:1.65. In some embodiments, the ratio of oil to surfactant is approximately 1:1.7. In some embodiments, the ratio of oil to surfactant is approximately 1:1.75. In some embodiments, the ratio of oil to surfactant is approximately 1:1.8. In some embodiments, the ratio of oil to surfactant is approximately 1:1.85. In some embodiments, the ratio of oil to surfactant is approximately 1:1.9. In some embodiments, the ratio of oil to surfactant is approximately 1:1.95. In some embodiments, the ratio of oil to surfactant is approximately 1:2. In some embodiments, the ratio of oil to surfactant is approximately 1:2.5. In some embodiments, the ratio of oil to surfactant is approximately 1:3. In some embodiments, the ratio of oil to surfactant is approximately 1:3.5. In some embodiments, the ratio of oil to surfactant is approximately 1:4. In some embodiments, the ratio of oil to surfactant is approximately 1:4.5. In some embodiments, the ratio of oil to surfactant is approximately 1:5.

In some embodiments, the aqueous dispersion medium (e.g., water, buffer, salt solution, etc.) and surfactant are utilized at a ratio ranging between 0.01 and 20. In some embodiments, the aqueous dispersion medium (e.g., water, buffer, salt solution, etc.) and surfactant are utilized at a ratio ranging between 0.1 and 20. In some embodiments, the aqueous dispersion medium (e.g., water, buffer, salt solution, etc.) and surfactant are utilized at a ratio ranging between 0.5 and 10. In some embodiments, the aqueous dispersion medium (e.g., water, buffer, salt solution, etc.) and surfactant are utilized at a ratio ranging between 0.5 and 1. In some embodiments, the ratio of aqueous dispersion medium (e.g., water, buffer, salt solution, etc.) to surfactant is approximately 0.01:1, approximately 0.02:1, approximately 0.03:1, approximately 0.04:1, approximately 0.05:1, approximately 0.06:1, approximately 0.07:1, approximately 0.08:1, approximately 0.0:1, approximately 0.1:1, approximately 0.2:1, approximately 0.3:1, approximately 0.4:1, approximately 0.5:1, approximately 1:1, approximately 2:1, approximately 3:1, approximately 4:1, approximately 5:1, approximately 6:1, approximately 7:1, approximately 8:1, approximately 9:1 or approximately 10:1. In some embodiments, the ratio of surfactant to water is approximately 0.5:1, approximately 1:1, approximately 2:1, approximately 3:1, approximately 4:1, approximately 5:1, approximately 6:1, approximately 7:1, approximately 8:1, approximately 9:1, approximately 10:1, approximately 11:1, approximately 12:1, approximately 13:1, approximately 14:1, approximately 15:1, approximately 16:1, approximately 17:1, approximately 18:1, approximately 19:1, or approximately 20:1. In some embodiments, aqueous dispersion medium (e.g., water, buffer, salt solution, etc.) and surfactant are utilized at a ratio ranging between 0.5 and 2. In some embodiments, the ratio of aqueous dispersion medium (e.g., water, buffer, salt solution, etc.) to surfactant is approximately 0.5:1, approximately 1:1, or approximately 2:1. In some embodiments, the ratio of surfactant to aqueous dispersion medium (e.g., water, buffer, salt solution, etc.) is approximately 0.5:1, approximately 1:1, or approximately 2:1. In some embodiments, the ratio of aqueous dispersion medium (e.g., water, buffer, salt solution, etc.) to surfactant is approximately 1:1. In some embodiments, compositions utilizing such ratios of aqueous dispersion medium (e.g., water, buffer, salt solution, etc.) to surfactant comprise water-in-oil emulsions.

The present invention also provides for particular cream and/or lotion compositions that are particularly effective and/or useful in medical contexts, e.g., for therapeutic purposes. The present invention encompasses the recognition that certain cream and/or lotion formulations are particularly useful and/or effective for topical administration of agents to a subject in need thereof. In some embodiments, the present invention provides certain cream and/or lotion formulations.

In some embodiments, known therapeutic agents and/or independently active biologically active agents are admixed with a cream and/or lotion formulation for preparation of a topical pharmaceutical composition.

In some embodiments, a cream and/or lotion formulation comprises purified water. In some embodiments, a cream and/or lotion formulation comprises methylparaben. In some embodiments, a cream and/or lotion formulation comprises mineral oil. In some embodiments, a cream and/or lotion formulation comprises isopropyl myristate. In some embodiments, a cream and/or lotion formulation comprises white petrolatum. In some embodiments, a cream and/or lotion formulation comprises emulsifying wax. In some embodiments, a cream and/or lotion formulation comprises propylparaben. In some embodiments, a cream and/or lotion formulation comprises pemulen. In some embodiments, a cream and/or lotion formulation does not comprise pemulen.

In some embodiments, a cream and/or lotion formulation comprises purified water, methylparaben, mineral oil, isopropyl myristate, white petrolatum, emulsifying wax, and propylparaben. In some embodiments, a cream and/or lotion formulation consists essentially of purified water, methylparaben, mineral oil, isopropyl myristate, white petrolatum, emulsifying wax, and propylparaben. In some embodiments, a cream and/or lotion formulation consists of purified water, methylparaben, mineral oil, isopropyl myristate, white petrolatum, emulsifying wax, and propylparaben.

In some embodiments, white petrolatum is or comprises a petrolatum agent selected from the group consisting of white petrolatum, wool wax, lanolin, Vasoliment, VASELINE® brand petroleum jelly, Saxoline, petroleum jelly, mineral jelly, mineral fat, mineral wax, paraffin jelly, yellow petrolatum, 2,6,10,15,19,23-hexamethyltetracosane, dodecahydrosqualene, perhydrosqualene, squalane, white VASELINE®, White Protopet, Ultima White, Snow White, a substance corresponding to CAS number 8009-03-8, and/or combinations thereof.

In some embodiments, a mineral oil is or comprises a mineral oil agent selected from the group consisting of paraffinic oils (e.g., oils based on n-alkanes), naphthenic oils (e.g., oils based on cycloalkanes), aromatic oils (e.g., oils based on aromatic hydrocarbons), and/or combinations thereof.

In some embodiments, an emulsifying wax is or comprises emulsifying wax NF (e.g., Spectrum Chemical catalog number W1026).

In addition, one such anti-hyper-hydrosis composition comprises each of these components; water, alcohol, aluminum sesquichlorohydrate, hydroxypropyl methyl cellulose, polysorbate 20, isopropyl myristate, eucalyptus oil, silicone oil, alkyl benzoate, glycerine, talc, a hydrophillic silica and a hydrophobic silica, phenoxyethanol, ethylhexyl glycerine, and citric acid. wherein the talc is replaced with arrowroot.

Also, a method for making one such composition comprises;
(viii) adding purified and/or deionized and/or distilled water to a vessel with the necessary amounts and concentrations of NaOH and/or HCl or citric or acetic acid or other base or acid to raise or lower the pH of the water to 8.5 (±0.1);
(ix) adding hydroxypropyl cellulose powder to a vessel and stir a resulting solution until the powder is fully hydrolyzed;
(x) lowering the pH of the solution to 7.0 (±0.1) using a 1N HCl solution and begin rapid mixing;
(xi) adding Polysorbate 20 as an emulsifier for stabilizing oils during mixing
(xii) adding aluminum sesquichlorohydrate during mixing, thereby lowering the pH of the solution
(xiii) adding silicone oil during mixing and ensuring viscosity of the solution does not exceed 200 centipoise;
(xiv) adding isopropyl myristate during mixing;
(viii) adding alkyl benzoate during mixing;
(ix) adding eucalyptus oil during mixing;
(x) adding glycerine during mixing;
(xi) adding talc and/or arrowroot during mixing;
(xii) adding hydrophobic silica slowly during mixing to avoid funing of fumed silica into the atmosphere;
(xiii) raising mixing speed once full amount of the hydrophobic silica is added to the solution;
(xix) adding a combination of phenoxyethanol and ethylhexyl glycerine as a preservative;
(xx) adding hydrophilic silica in the same manner as steps (xii) and (xiii);
and;
completing the composition by mixing until the composition is a stable homogeneous cream-like consistency.

Those skilled in the art will recognize, or be able to ascertain using no more than routine experimentation, many equivalents to the specific embodiments of the invention described herein.

The scope of the present invention is not intended to be limited to the above Description, but rather is as set forth in the following claims:

We claim:
1. An anti-sweating composition consisting of,
water,
alcohol,
aluminum sesquichlorohydrate,
hydroxypropyl methyl cellulose,
polysorbate 20, isopropyl myristate,
eucalyptus oil,
silicone oil,
alkyl benzoate,
vegetable derived glycerine,
arrowroot,
talc,
a silica component selected from a hydrophilic silica, a hydrophobic silica, and a mixture thereof,
a preservative blend selected from a mixture of phenoxyethanol and ethylhexyl glycerine or a mixture of phenoxyethanol, chlorphenesin and caprylyl glycol,
and optionally citric acid.

2. The composition of claim 1, wherein said silica component is hydrophobic silica.

3. The composition of claim 1, wherein silica component is hydrophilic silica.

4. The composition of claim 2, wherein said hydrophilic silica is a hydrophilic fumed silica and said hydrophobic silica is a hydrophobic fumed silica.

5. The composition of claim 1, wherein said silicone oil is polydimethyl siloxane (PDMS).

6. The composition of claim 1, wherein said alcohol is 2-propanol.

7. The composition of claim 1, wherein said alkyl benzoate is C12-C15 alkyl benzoate.

8. The composition of claim 1, wherein said composition is a group of components consisting of a weight percent of each component as follows; 37-39 percent water, 11-12 percent 2-propanol, 14-15 percent aluminum sesquichlorohydrate, 12-13 percent hydroxypropyl methylcellulose, 4-5 percent polysorbate 20, 0.5-1.0 percent isopropyl myristate, 0.5-2.0 percent eucalyptus oil, 0.5-1.5 percent polydimethyl siloxane, 1.0-2.0 percent alkyl benzoate, 0.5-1.0 percent vegetable derived glycerine, 0.1-5 percent arrowroot, 1.0-3.0 percent talc, 5.0-7.0 percent hydrophilic silica, 4.0-6.0 percent hydrophobic silica, 0.5-1.0 percent of a combination of phenoxyethanol and ethylhexyl glycerine.

9. The composition of claim 4, wherein said preservative blend is a mixture of phenoxyethanol, chlorphenesin, and caprylyl glycol and is present at between 0.5 and 1.0 percent.

10. The composition of claim 8, wherein said composition is selected from the group consisting of: a lotion, a cream, a spray, a moisturizer, a balm, a paste, and a saline solution.

11. The composition of claim 8, wherein said composition is non-irritating and leaves no residue.

* * * * *